(12) United States Patent
Wörtche et al.

(10) Patent No.: US 9,880,143 B2
(45) Date of Patent: Jan. 30, 2018

(54) SENSOR SYSTEM, MOTE AND A MOTES-SYSTEM FOR SENSING AN ENVIRONMENTAL PARAMETER

(71) Applicant: INGU Solutions Inc., Waterloo (CA)

(72) Inventors: Heinrich Johannes Wörtche, Bedum (NL); Elena Talnishnikh, Amersfoort (NL); Johannes Hubertus Gerardus Van Pol, Groningen (NL)

(73) Assignee: INGU Solutions Inc., Calgary (CA)

( * ) Notice: Subject to any disclaimer, the term of this patent is extended or adjusted under 35 U.S.C. 154(b) by 0 days.

(21) Appl. No.: 14/641,285

(22) Filed: Mar. 6, 2015

(65) Prior Publication Data

US 2015/0268213 A1 Sep. 24, 2015

(30) Foreign Application Priority Data

Mar. 20, 2014 (NL) ...................... 2012484

(51) Int. Cl.
*G01N 33/18* (2006.01)
*H02J 7/02* (2016.01)
(Continued)

(52) U.S. Cl.
CPC .......... *G01N 33/1886* (2013.01); *G01D 9/02* (2013.01); *H02J 7/025* (2013.01); *H02J 7/34* (2013.01);
(Continued)

(58) Field of Classification Search
CPC ........ G01N 33/1886; H02J 7/025; H02J 7/34; H02J 7/345; G01D 9/02
(Continued)

(56) References Cited

U.S. PATENT DOCUMENTS 8,330,603 B1 * 12/2012 Gibb ................... G01F 23/266
340/602
2005/0197198 A1 * 9/2005 Otten ................ A63B 69/3614
473/221
(Continued)

FOREIGN PATENT DOCUMENTS

GB 2486008 A 6/2012
WO 0203856 A2 1/2002

OTHER PUBLICATIONS

Search Report and Written Opinion of the Dutch Patent Application No. NL2012484 dated Nov. 10, 2014.
(Continued)

*Primary Examiner* — Hezron E Williams
*Assistant Examiner* — Marrit Eyassu
(74) *Attorney, Agent, or Firm* — Bereskin & Parr LLP

(57) ABSTRACT

The invention provides a sensor system, mote and a motes-system. The sensor system is configured for being contained in a container having a maximum outer dimension less than 10 millimeter and for sensing at least one environmental parameter (T, P, pH, ρ). The sensor system includes at least one sensor configured for measuring the at least one environmental parameter and for generating a sensed value (xT, xP). The sensor system includes a storage element and a timer in which the at least one sensor is configured to measuring the at least one environmental parameter at each time triggers (t1, t2, . . . ) from the timer and for storing a sensed value (xT, xP). The sensor system further includes an energy storage comprising a chargeable capacitor being chargeable via electro-magnetic radiation of a predefined frequency, and wherein the sensor system is configured to initiate a sequence of sensed values when the energy storage is charged or is being charged.

17 Claims, 6 Drawing Sheets

(51) Int. Cl.
*H02J 7/34* (2006.01)
*H02J 50/80* (2016.01)
*H02J 50/40* (2016.01)
*H02J 50/20* (2016.01)
*G01D 9/02* (2006.01)

(52) U.S. Cl.
CPC .............. *H02J 50/20* (2016.02); *H02J 50/40* (2016.02); *H02J 50/80* (2016.02); *H02J 7/345* (2013.01)

(58) Field of Classification Search
USPC ........................................................ 73/53.01
See application file for complete search history.

(56) References Cited

U.S. PATENT DOCUMENTS

| | | | |
|---|---|---|---|
| 2006/0238422 A1 | 10/2006 | Schantz et al. | |
| 2007/0083174 A1* | 4/2007 | Ales, III | A61F 13/42 604/361 |
| 2007/0117392 A1* | 5/2007 | Smith | H01L 21/84 438/689 |
| 2007/0139000 A1* | 6/2007 | Kozuma | H02J 5/005 320/108 |
| 2007/0272011 A1* | 11/2007 | Chapa, Jr. | A63B 24/0006 73/379.01 |
| 2008/0061967 A1* | 3/2008 | Corrado | G06K 7/10079 340/539.26 |
| 2008/0252254 A1* | 10/2008 | Osada | H01M 10/0436 320/108 |
| 2010/0223988 A1* | 9/2010 | Crow | E21B 41/0064 73/152.04 |
| 2013/0274567 A1 | 10/2013 | Grosser et al. | |
| 2016/0308404 A1* | 10/2016 | Tsai | G01R 31/42 |

OTHER PUBLICATIONS

Dubbelman, G., Duisterwinkel, E., Demi, L., Talnishnikh, E., Wortche, H.J. & Bergmans, J.W.M. (2014). Robust sensor cloud localization from range measurements. Conference Paper : Proceedings of the IEEE/RSJ International Conference on Intelligent Robots and Systems (IROS), Sep. 14-18, 2014, Chicago, Illinois, (pp. 3820-3827).

Duisterwinkel, E., Demi, L., Dubbelman, G., Talnishnikh, E., Wörtche, H.J. & Bergmans, J.W.M. (2014). Environment mapping and localization with an uncontrolled swarm of ultrasound sensor motes. Conference Paper : Proceedings of the 166th Meeting of the Acoustical Society of America, Dec. 2-6, 2013, San Fransisco, California.

* cited by examiner

400

410

| | |
|---|---|
| 0 | 273 |
| 1 | 273 |
| 2 | 373 |
| 3 | 373 |
| 4 | 353 |
| 5 | 347 |
| 6 | 342 |
| ... | ... | time1 → row 0; time2 → row 1; $x_T$ → 273

Fig. 5

SENSOR SYSTEM, MOTE AND A MOTES-SYSTEM FOR SENSING AN ENVIRONMENTAL PARAMETER

CROSS REFERENCE TO RELATED APPLICATION

This application claims the priority benefit under 35 U.S.C. § 119 of Netherlands Patent Application No. 2012484, filed on Mar. 20, 2014, which is hereby incorporated in its entirety by reference.

FIELD OF THE INVENTION

The invention relates to a sensor for mapping an environmental parameter. The invention further relates to a mote and a motes-system.

BACKGROUND ART

Sensors for sensing an environmental parameter are well known and used throughout our current environment. Only one of the many examples used in today's world may, for example, be a temperature sensor which may, for example, be applied in a car for providing temperature information to the driver of the car or to the on-board computer of the car. Such a sensor draws its power from the overall power system of the car and uses the on-board wiring to provide the sensed value to the display of the car or to the on-board computer. However, when sensing the environmental parameters in a remote location, the requirements to the sensor system are quite different.

Sensor systems having such requirements are, for example, used in a sensor mote. A sensor mote typically refers to a relatively small sensor with its own energy storage. Also typically the sensor mote is part of a wireless network via which the sensed environmental parameter is communicated to a remote computer. A motes-system is a plurality of sensor motes which together form a plurality of sensors for sensing the environmental parameter. Such motes-systems have been used in many diverse applications, from earthquake measurements to warfare.

Such known motes typically comprises a controller, transceiver, power source and one or more sensors. One example of environmental monitoring can be found in the NASA sensor web. This network comprises spatially distributed sensors that wirelessly communicate with each other. In this network, every mote sends out collected data to every other mote, so substantially every mote knows what is happening in the network. Alternatively, sensor networks may be configured to use GPS communication and/or may be configured to handle "Big" data sets.

Using such known sensor networks for environmental mapping or monitoring, the position of the individual motes should be known which requires extensive communication with the outside world, for example, via a Global Positioning System (further also indicated as GPS). However, in some remote environments, such as, for example, oil wells or sewer systems in cities, the GPS signal does not reach the individual motes and other means of measuring the environment parameter have to be found.

SUMMARY OF THE INVENTION

One of the objects of the invention is to provide a sensor system which is capable of detecting one or more environmental parameters during predefined time duration and which can be used in remote environments.

A first aspect of the invention provides a sensor system according to claim 1. A second aspect of the invention provides a mote according to claim 13. A third aspect of the invention provides a motes-system according to claim 14. Embodiments are defined in the dependent claims.

The sensor system in accordance with the first aspect of the invention is configured for being contained in a container having a maximum outer dimension less than 10 millimeter and for sensing at least one environmental parameter. The sensor system comprises at least one sensor configured for measuring the at least one environmental parameter and for generating a sensed value representing the at least one environmental parameter. The sensor system further comprises a storage element for storing the sensed value and a timer for generating a plurality of time triggers separated by a predetermined time interval, whereby the at least one sensor is configured for measuring the environmental parameter substantially at the time of each of the time triggers and for generating a corresponding sensed value. The sensed value is subsequently stored onto the storage element to generate a sequence of sensed values. The sensor system further comprises an energy storage for supplying at least the at least one sensor, timer and storage element with power to enable operation of the sensor system during a predefined time duration. The energy storage comprises a chargeable capacitor being chargeable via electro-magnetic radiation of a predefined frequency and the sensor system is further configured to initiate the sequence of sensed values when the energy storage is charged or when the energy storage is being charged. The sensor system also comprises an antenna for receiving the electro-magnetic radiation for charging the energy storage.

The inventors have realized that the requirements of a sensor system able to measure an environmental parameter for some predefined time duration at a remote environment are very specific. Such remote environment may, for example, be underground reservoirs, for example, used in mining or oil and gas industry. Alternatively, the remote environment may be a sewer system and/or (underground) water supply system or a subterranean river. First the dimensions of the sensor system should be such that it will fit in a container having its outer dimensions less than 10 millimeter. Especially in sewer systems and other underground reservoirs, such dimensions are required to ensure that the sensor system may migrate efficiently through the sewer system or through the channels inside an underground reservoir to be able to sense the at least one environmental parameter. Having a container with a maximum outer dimension of less than 10 millimeter would require the sensor system to have a maximum outer dimension of, for example, less than 7 millimeter. Such container may have a substantially spherical shape having an outer dimension of 10 millimeter or may have a substantially cylindrical shape in which the maximum outer dimension along the longitudinal axis of the cylindrical shape is less than 10 millimeter. The container is required to protect the sensor system from the often harsh environment that is present in these remote environments. The container may be made from any suitable material and may also be produced by melting the material, submerge the sensor system into the molten material and let the molten material harden to enclose and contain the sensor system inside the container. Such molten material may, for example, be a suitable plastic material, possibly reinforced. The suitability of the material of the container is depending on the environment in which the sensor system is to operate and is depending on further requirements of the sensor system, such as the buoyancy of the sensor system contained in the container in the liquid of the environment.

The mote is particularly useful for mapping an unknown environment. The motes do not rely on external location references, absolute or relative. In particular a static Wireless Sensor Network (WSN) is not needed. Standard triangulation methods are also not needed.

In an embodiment, a mote is configured for at least one frequency of multiple frequencies. The mote comprises a transmitter and a receiver. The transmitter is configured to emit an electromagnetic pulse at said configured frequency, the receiver being configured to receive pulses send at frequencies of the multiple frequencies other than the configured frequency. Transmitter and receiver are configured to alternate sending and receiving of the pulse. From the received pulse recorded at the mote the unknown environment may be reconstructed, e.g., mapped. See Dutch patent application N2011892, incorporated herein by reference, for more information on, e.g., how sending and receiving pulses may map an unknown environment.

To allow the sensor system to operate for the predefined time duration—which typically is a few days—in the remote environments while contained in such small container, also the requirements to the energy storage are rather constrained such that standard batteries may not be useable. In addition, any energy consumption should be minimized. As such, the inventors have designed a specific sensor system architecture in which the energy storage comprises a chargeable capacitor which may be charged via electro-magnetic radiation received via the on-board antenna. Subsequently the sensor system is configured for initiating the sequence of sensed values when the energy storage is charged or when the energy storage is being charged. This combination of features allows an appropriate charging of the energy storage of the sensor system and also allows for a time calibration of the sensed environmental parameter at the time the energy storage is being charged or is (fully) charged. This omits the need for an activation switch or for a control signal for initiating the sequence of sensed values. For example, the timer may be initiated when the energy storage is more than 10% charged, or more than 50% charged or more than 80% charged. So the sensor system may be automatically activated while the energy storage is being charged. Using the sequence of sensed values, together with the predetermined time interval between subsequent time triggers (and so between subsequent sensed values in the sequence of sensed values) and the initiation time at which the sequence of sensed values has been started (triggered by the energy storage being charge or is fully charged), the exact time at which each of the sensed values is sensed by the sensory system can be determined sufficiently accurate and relatively easy.

A further benefit when using the sensor system according to the invention is that the claimed configuration may also be used to enable an easy synchronization of the sensor system to other similar sensor systems. The synchronization is almost automatically done when, for example, each sensor system is simultaneously charged, for example, when all sensor systems at the same time are subject to the same electro-magnetic radiation for charging the on-board energy storage of each of the sensor systems. As indicated in the sensor system according to the invention, the sensor system is configured to initiate the sequence of sensed values when the energy storage is charged or when the energy storage is being charged. When each of the similar sensor systems are further configured to have the same predetermined time interval between subsequent time triggers, the plurality of similar sensor systems all measure their sensed values (representing their specific environmental parameter) substantially at the same time. So each corresponding sensed value in the sequence of sensed values in each of the similar sensor systems that have been charged using the same electro-magnetic radiation is sensed substantially at the same time. The similar sensor systems may have similar configuration as the sensor system according to the invention, but may, for example, sense a different environmental parameter compared to the sensor system. For example, the sensor system according to the invention may sense an ambient temperature around the sensor system during the predefined time duration, while some of the similar sensor systems may, for example, sense an ambient pressure surrounding the similar sensor system during the predefined time duration. When the sensor system together with the similar sensor systems migrate through the remote environment some information about the environmental parameter along the route taken by the sensor system and by the similar sensor system may be analyzed. So when using a plurality of such sensor systems, the design of the sensor system according to the invention enables to get synchronized readings from each of the plurality of sensor systems of their environmental parameters and allows a very small efficient sensor system which can migrate through narrow passage ways in the remote environment and which is chargeable.

In an embodiment of the sensor system, the sensor system is configured to reset the timer for generating a new plurality of time triggers when the energy storage is charged or when the energy storage is being charged. This allows the sensor system to be re-used to generate a next sequence of sensed values as soon as the energy storage is charge or is being charged.

In an embodiment of the sensor system, the timer comprises an oscillator and a counter and wherein the resetting of the timer comprises resetting the counter. The oscillator may be any oscillator useable for generating a sequence of triggers separated by the predefined time interval in an electronic circuit, including, for example, a quartz oscillator. However, in view of the dimension and power restrictions a relatively low-power logic oscillator circuit would be preferred.

In an embodiment of the sensor system, the sensor system is configured for storing a trigger number together with each sensed value, the trigger number being generated by the timer and indicating the number of time triggers generated by the timer since the resetting of the timer. The trigger number may, for example, be generated by the counter. Using such trigger number and storing the trigger number together with the sensed value in the storage element allows an improved identification of the timing of the sensed value. Using the trigger number, the timing of the sensed value is not only defined by its place in the sequence of sensed values, but is also defined by the associated trigger number stored together with the sensed value.

In an embodiment of the sensor system, the sensor system further comprises a controller for controlling the operation of the sensor system. In an embodiment of the controller, the controller is a state machine. In general, a state machine as used in embodiments of this invention is any device that stores a status or value of something at a given time. In a more advanced version of the controller or state machine, the controller or state machine may be able to receive input and may use this input to change the status or way of working of the system dependent on the received input. A state machine may be preferred as controller because such state machines often comprise only a limited number of logic circuits, often dedicated to the required controlling, such that a minimal amount of energy and space is required. Of course if energy and space limitations allow, also other types of controllers may be used in the sensor systems according to the invention. The controller used in the embodiment of the invention may, for example, ensure that the sensor takes a sensed value at each time trigger generated by the timer and that the sensed value (possibly including the trigger number) is subsequently stored in the storage element. The storage element may, for example, be a shift register in which the sensed values are sequentially stored as they are measured by the sensor. Using such a controller and shift register in the sensor system according to the current invention, the sensor system may be miniaturized and produced at a relatively low cost. Due to these small dimensions and relatively low cost, such sensor systems are specifically beneficial when used in a swarm of sensor systems which swarm the remote environment and sense environmental parameters at each of their individual locations within the remote environment.

In an embodiment of the sensor system, the controller is constituted of one or more logic blocks. As indicated before, the relatively stringent dimension requirements to enable the sensor system to move through narrow passageways in, for example, sewer systems or oil wells, together with the power requirements to enable operation during the predefined time duration also require the controller to have very small dimensions and very low power consumption. Constituting the controller of a few logic blocks would minimize the power required to run the sensor system and would allow the sensor system, including controller, to be contained in such small containers.

Alternatively, when power and dimension requirements are met to allow the sensor system to operate during the predefined time duration, any controller system or microcontroller may be used in the sensor system.

In an embodiment of the sensor system, the controller is coupled to the antenna and is configured to communicate via the antenna. Using the antenna both for charging the energy storage and for communication of the controller with the outside further reduces the overall elements required to allow the sensor system to function, which further contributes to the miniaturization of the sensor system. Furthermore, no connectors are necessary for connecting the controller or any other element of the sensor system to the outside. So both the charging and communication is done wirelessly using the same antenna to further enable cost reduction and miniaturization.

In an embodiment of the sensor system, the controller is configured for communicating the stored sensed values. When the sensor system has been working in the remote environment and has been harvested back from the remote environment, the controller may be triggered, for example, using a "release storage trigger" such that the sequence of sensed values, possibly together with the corresponding trigger number, is transmitted via the antenna. An external receiving system, for example, an external computer system, may be configured to capture the transmitted sequence of sensed values, for example, to enable data analysis.

In an embodiment of the sensor system, the controller is configured for receiving configurable parameters via the antenna for determining an operation of the sensor system. The sensor system may be configured using specific parameter settings which may, for example, be stored in the controller. Such parameter settings may, for example, be the duration of the predetermined time interval between two subsequent triggers and/or the predefined time duration during which the sensor system is operated. Typically, taking the measurements of the environmental parameter and storing the sensed value onto the storage element requires most of the energy consumed by the sensor system. As such configuring the predetermined time interval between two subsequent triggers also adapts the overall predefined time duration. Also the dynamics of the remote environment in which the measurements are taken may be important to capture. These dynamics also may define what the preferred duration of the predetermined time interval should be. Finally, when more than one sensor system is used for measuring the remote environment, some of the sensor systems may have different configurable parameters to be able to capture changes in the remote environment having different dynamics. For example, trying to capture local temperature variations may require different configurable parameters compared to capturing local pressure variations.

In an embodiment of the sensor system, the predetermined time interval is a configurable parameter. As indicated above, this predetermined time interval is important to configure the measurement sequence of the sensor system such that a good alignment is achieved between the dynamics of the variation of the sensed value in the remote environment and the speed at which data is retrieved by the sensor system.

In an embodiment of the sensor system, the environmental parameter is selected from a list comprising at least: temperature and pressure, acidity and conductivity. The sensor system may comprise more than one sensor for sensing different environmental parameters. However, in view of the constrained dimension requirements and the predefined time duration during which the sensor system is expected to operate, the sensor system may comprise only a single sensor.

In an embodiment of the sensor system, the predefined time duration is at least 24 hours. Often 24 hours is a minimum to be able to measure a parameter in a remote environment. More preferably, the predefined time duration may be more, for example, 36 hour, 48 hours or even 72 hours. From experience the inventor gathered that an operation for 72 hours is often enough to be able to monitor remote environments while still taking a considerable amount of sensed values.

The mote in accordance with the second aspect of the invention comprises the sensor system according to any of the previous embodiments contained in the container, wherein the mote is buoyant in a predefined liquid. To ensure that the mote comprising the sensor system migrates through the remote environment, the mote comprising the sensor system is buoyant in the predefined liquid. The predefined liquid may, for example, be water, or, for example, water containing a predetermined amount of salt, or, for example, oil. When the mote is used to monitor an oil well, it may be injected at one point into the oil well and may be harvested at some later time together with the crude oil harvested from the oil well. In such a way, the mote comprising the sensor system will be able to generate a sequence of sensed values during the transition from the injection point to the harvesting point. This sequence of sensed environmental parameters will provide additional information about the underground reservoir or other remote environment. Alternatively, the mote comprising the sensor system may be injected into a sewer system at some stage and harvested further downstream. Again, the sequence of sensed values provides additional information about the sewer system. Known motes which are, for example, used the NASA sensor web typically communicate with other motes to form a mote network. The mote according to the invention is different in the sense that it is not initially configured to communicate the sensed environmental parameter to other motes but to store the sensed environmental parameter inside the mote to be harvested later. This is chosen to ensure the long pre-defined time duration during which the mote should be able to be active in the remote environment as wireless communication typically requires much energy. If, however, some communication between the different motes is required and energy storage is sufficient, communication may be added to the mote.

The motes-system in accordance with the third aspect of the invention comprises a plurality of motes according to the invention, wherein each of the sensor systems in each of the plurality of motes are chargeable using electro-magnetic radiation having the same predefined frequency. Using the plurality of motes and sending the plurality of motes through the same remote environment, a distribution of the sensed environmental parameter can be determined which also provides input about the overall remote environment. For example, when injecting the plurality of motes into an oil well using hot water, the temperature variation inside the individual motes provide an indication how far the individual mote has moved away from the main water stream through the oil well. Together with the time it takes from injection and harvesting of the individual mote, this temperature variation provides a measure about the extent of the oil well. To register the time at which the mote is harvested, the mote may simply be placed inside a tank containing liquid at a specific predefined temperature, for example, in a tank containing ice-water (having a temperature of 0 degrees Celsius).

In an embodiment of the motes-system, the plurality of motes are synchronized when the energy storage of each of the sensor systems is charged or when the energy storage of each of the sensor systems is being charged. When, for example, a plurality of motes is synchronized and substantially simultaneously injected into an oil-well, the plurality of motes will provide information on the sensed environmental parameter from each of the harvested motes. Probably some of the motes will be lost, but for the motes harvested during the harvesting of the crude oil, the sequence of sensed values provide some indication of the variation of the environmental parameter while the mote is traveling through the well. Because each of the motes in the motes-system are synchronized the sequence of sensed values are all taken at substantially the same time. So each of the $20^{th}$ sensed value in the sequence of sensed values are measured by each of the motes in the motes-system at the same time—taking any variations of the predetermined time interval between the time triggers into account.

BRIEF DESCRIPTION OF THE DRAWINGS

These and other aspects of the invention are apparent from and will be elucidated with reference to the embodiments described hereinafter. In the drawings, FIG. 5 shows possible data content of the storage element of a sensor system according to the invention.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
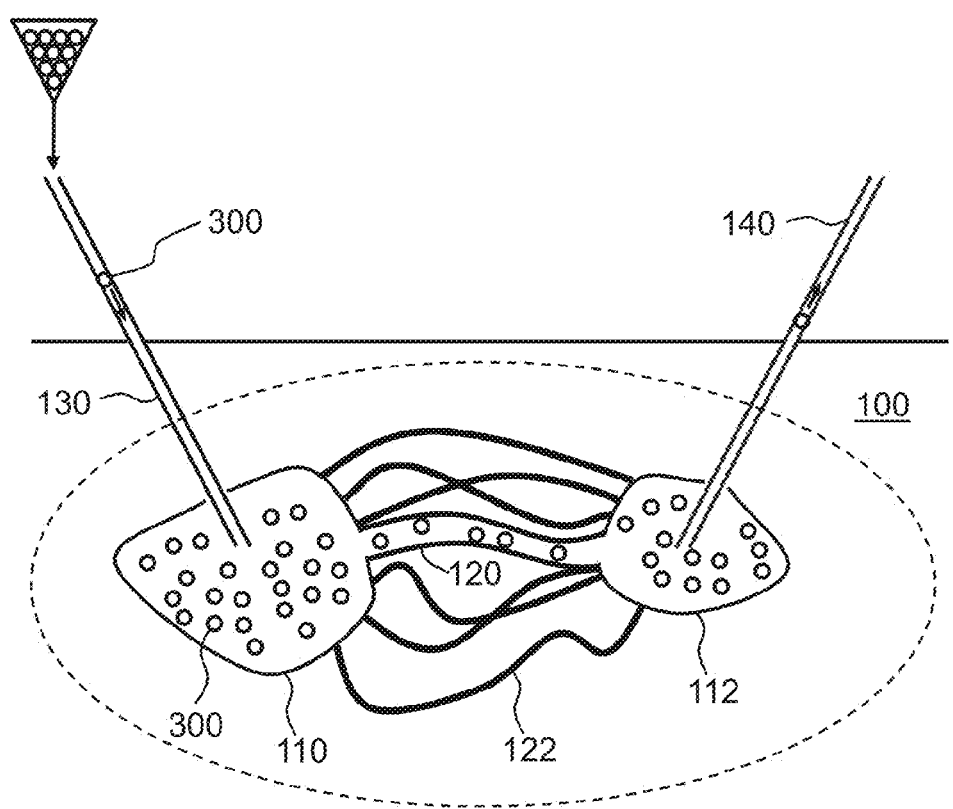
FIG. 1 shows a remote environment, in which an environmental parameter is sensed using a plurality of motes according to the invention.

FIG. 1 shows an environment 100 in which a mapping is required. The environment 100 shown in FIG. 1 represents an oil well 100 having a first cavity 110 which is connected to a second cavity 112 via a main passageway 120 and a plurality of smaller passageways 122. FIG. 1 further shows a plurality of motes 300 which are injected via an injection pipe 130 and which may be harvested via an extraction pipe 140. The motes 300 contain a sensor system 200A, 200B (see FIGS. 2A and 2B) which are contained in a spherical container (see FIG. 4A). Each of the motes 300 may, for example, be injected into the oil well 100 via the injection pipe 130 using a stream of hot water (not shown) which may, for example, be used to dilute some of the treacle cured oil to allow more of the treacle crude oil to be harvested. The stream of hot water typically has a temperature close to the boiling temperature of water. The motes 300 are designed to float or be buoyant in the injected liquid such that the motes 300 may migrate through the oil well via the injected liquid and such that some of the motes 300 may be harvested from the oil well 100 via the extraction pipe 140 together with the harvested crude oil or together with the extracted water. When the sensor system 200A, 200B inside the mote 300 is sensing the environmental temperature by creating a sequence of sensed temperature values $x_T$ (see FIG. 5), the variation in the sequence of the sensed temperature $x_T$ together with the overall time the motes 300 migrate through the well provide an indication about the extent of the oil well and whether the mote 300 migrated via the main passage way 120 from the injection pipe 130 to the extraction pipe 140 or via any of the smaller passageways 122.

As indicated above, the motes 300 are preferably designed to float or be buoyant in the injected liquid. Floating or buoyancy is achieved when the volumetric mass density of a mote 300 substantially equals the volumetric mass density of the liquid. This ensures that the motes 300 preferably neither sink in the liquid nor rise; as a result the motes 300 will more easily enter all parts of the remote environment 100.

In an alternative embodiment, the motes 300 which are injected into the remote environment are separated in different dimension groups (not shown), in which each mote 300 in a specific dimension group has predefined external dimension different from the motes from a different specific dimension group. As such, motes 300 having different dimensions are injected into the remote environment which now also enables to capture some information about the dimensions of the smaller passageways 122 that may be present inside the remote environment 100.

Due to the overall small dimensions of the motes 300, the motes 300 may migrate relatively easily through the oil well 100 to provide information related to the extent of the oil well 100. Furthermore, using low energy consuming elements in the sensor system 200A, 200B enables the motes 300 according to the invention to migrate through the remote environment for more than 72 hours, which enables a mapping of relatively large remote environments 100.

As indicated before, the remote environment 100 may, for example, be an underground reservoir 100, for example, used in mining or oil and gas industry. Alternatively, the remote environment 100 may be a sewer system 100 and/or (underground) water supply system 100 or subterranean river 100.

Figure 2A:
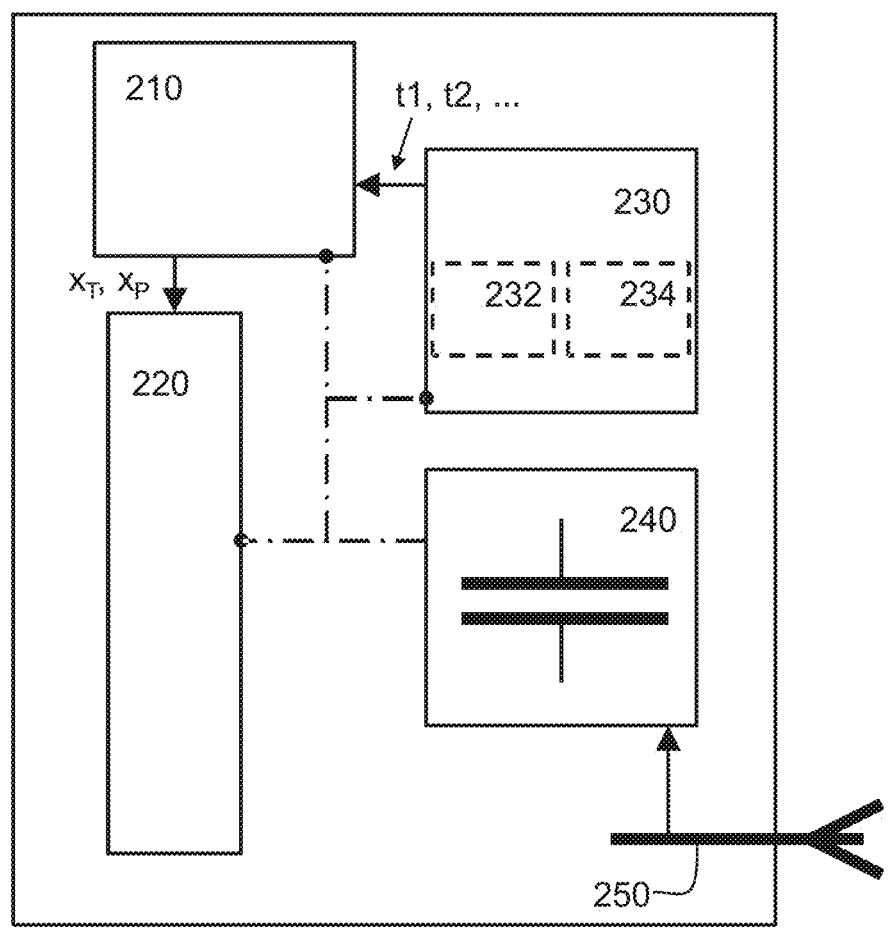
FIG. 2A shows a first embodiment of a sensor system according to the invention.

FIG. 2A shows a first embodiment of a sensor system 200A according to the invention. The sensor system 200A comprises a sensor 210 for measuring or sensing an environmental parameter T, P, pH, ρ and for generating the sensed value $x_T$, $x_P$ (see FIG. 5) representing the value of the sensed environmental parameter T, P, pH, ρ. The environmental parameter T, P, pH, ρ may, for example, be the ambient temperature T surrounding the sensor system 200A or may, for example, be the ambient pressure P surrounding the sensor system 200A or an acidity pH of the surroundings of the sensor system 200A or the conductivity ρ of the surroundings of the sensor system 200A. The sensor system 200A further comprises a storage element 220 for storing the sensed values $x_T$, $x_P$ in a sequence of sensed values $x_T$, $x_P$. The storage element 220 may, for example, be a shift register 220 for storing the sequence of sensed values $x_T$, $x_P$. The benefit when using such a shift register 220 as storage element 220 is that they typically may be produced relatively small and consume relatively little energy. However, any other storage element 220 may be used which may be produced within the predefined dimensions of the sensor system 200A and which energy consumption is low enough to ensure the operation of the sensor system 200A for the predefined time duration. The sensor system 200A also comprises a timer 230 configured for generating a plurality of time triggers t1, t2 . . . separated by a predetermined time interval Δt. The sensor system 200A is configured that the sensor 210 measures the environmental parameter T, P, pH, ρ when receiving a time trigger t1, t2, . . . from the timer 230 and stores the sensed values $x_T$, $x_P$ sequentially in the storage element 220. Finally, the sensor system 200A comprises an energy storage 240 connected to an antenna 250. The energy storage 240 is configured for supplying the sensor 210, the storage element 220 and the timer 230 with energy during a predefined time duration—which is indicated in FIG. 2A using the dash-dotted connection lines between the energy storage 240 and the sensor 210, storage element 220 and timer 230. The energy storage 240, for example, comprises a capacitor 240 which preferably is connected to an antenna 250 such that the energy storage 240 may be charged via electro-magnetic radiation (not shown) captured by the antenna 250. As such, the sensor system 200A may be charged wirelessly.

The minimal design of the sensor system 200A as shown in FIG. 2A is capable of measuring the environmental parameter T, P, pH, ρ as soon as the energy storage 240 is charged or is being charged. As soon as the energy storage 240 is charged or is being charged, the timer 230 generates time triggers t1, t2, . . . separated by predetermined time intervals Δt. Each time the sensor 210 receives a time trigger t1, t2, . . . the sensor 210 senses the current ambient environmental parameter T, P, pH, ρ and generates a sensed value $x_T$, $x_P$. Each of these generated sensed values $x_T$, $x_P$ are sequentially stored in the storage element 220 to generate a sequence of sensed values $x_T$, $x_P$. Knowing the time at which the energy storage 240 is charged or is being charged defines the start of the sequence of sensed values $x_T$, $x_P$ and defines the exact time at which each of the sensed values $x_T$, $x_P$ in the sequence of sensed values $x_T$, $x_P$ are measured. Due to this architecture, relatively few on-board intelligence is necessary to allow the sensor system 200A according to the invention to gather and store the sequence of sensed values $x_T$, $x_P$, which enables a relatively small sensor system 200A which may operate during a significant predefined time duration in a remote environment.

Thus the timer may not only start measurements and initiating sensing but also creates synchronizations between the motes in the system. As such the system/plurality of INCAS3 motes can perform coherently as a system. In an embodiment, motes reset only the timer upon charging without affecting the memory unit. As a result re-charging does not affect the stored memory values. Upon re-charging the timer generates a new sequence of triggers or trigger numbers; new sensed values could be stored with the new trigger numbers (time1, time2, . . . ) without overwriting previously stored sensed values and trigger numbers. In this embodiment, a mote may be re-charged before reading out. The read-out may be done using the antenna. In an embodiment, the readout can be done before recharging. The readout function may be independent or not coupled to the re-charging.

When the energy storage 240 is exhausted, the sensor system 200A simply stops gathering the environmental parameter and awaits the time the sensor system 200A is harvested back from the remote environment. The data may be extracted from the storage element 220 in any known method, for example, by removing the sensor system 200A from the container and electronically connecting a data reader (not shown) to the storage element 220 for extracting the stored sequence of sensed values $x_T$, $x_P$. Using the sequence of sensed values $x_T$, $x_P$ from a plurality of sensor systems 200A, information about the remote environment 100 may be gathered.

The timer 230 shown in FIG. 2A may comprise an oscillator 232 and a counter 234. The oscillator 232 may be any oscillator 232 useable for generating a sequence of triggers t1, t2, . . . separated by the predefined time interval Δt in an electronic circuit, including, for example, a quartz oscillator. However, in view of the dimension and power restrictions a relatively low-power logic oscillator circuit 232 would be preferred. The counter 234 may be configured for generating a trigger number time1, time2, . . . for identifying individual triggers t1, t2, . . . generated by the oscillator 232. These trigger numbers time1, time2, . . . may be stored in the storage element 220 together with the sensed values $x_T$, $x_P$ to uniquely identify the time at which each of the sensed values $x_T$, $x_P$ in the sequence of sensed values $x_T$, $x_P$ are measured.

Figure 2B:
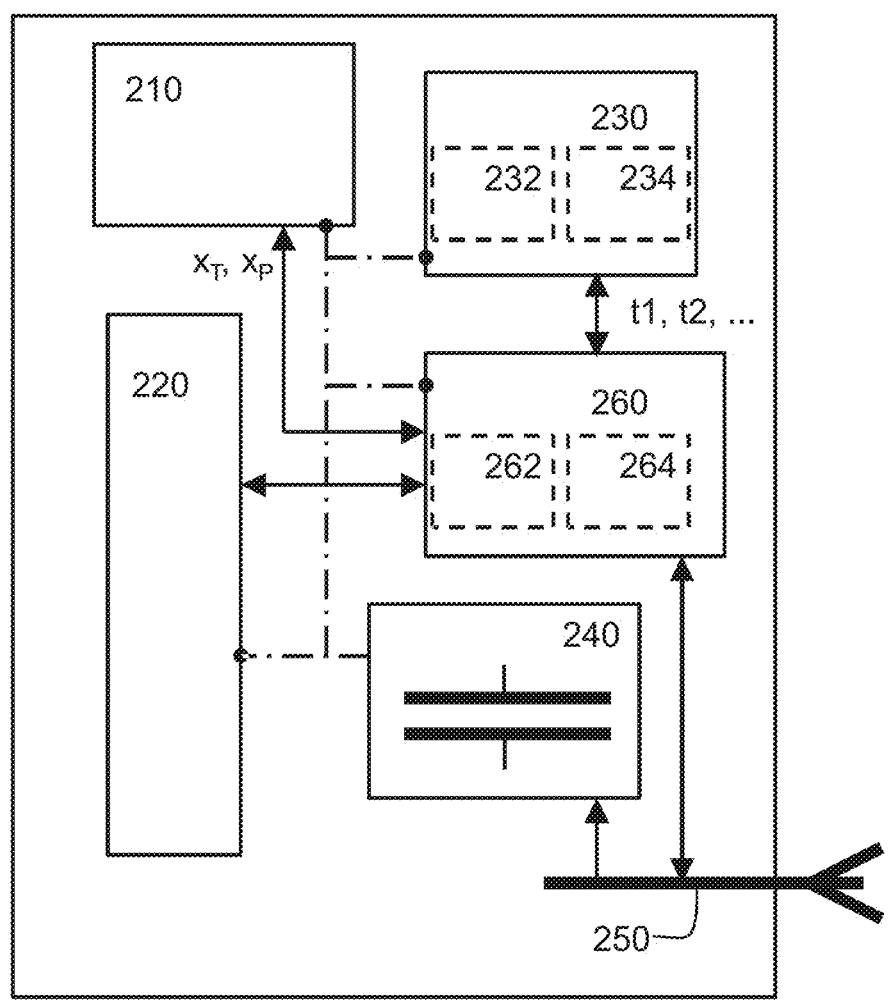
FIG. 2B shows a second embodiment of the sensor system according to the invention.

FIG. 2B shows a second embodiment of the sensor system 200B according to the invention. This second embodiment of the sensor system 200B also comprises a sensor 210 for sensing an environmental parameter T, P, pH, ρ and for generating a sensed value xT, xP to be stored in the storage element 220. This second embodiment of the sensor system 200B further comprises the timer 230 for generating time triggers t1, t2, . . . and the energy storage 240 connected to the antenna 250 for wirelessly charging the energy storage 240 via electro-magnetic radiation. In addition, this second embodiment of the sensor system 200B further comprises a controller 260 for controlling the operation of the sensor system 200B. The controller 260 may, for example, be a state machine 260 which represents any device that stores a status or value of something at a given time. In a more advanced version of the controller 260, the controller 260 may be able to receive input, for example, via the antenna 250 (which is illustrated by the double arrow connecting the controller 260 and the antenna 250 in FIG. 2B). The state machine 260 may in some embodiments be preferred as controller 260 because such state machines 260 often comprise only a limited number of logic circuits 262, 264, often dedicated to the required controlling, such that a minimal amount of energy and space is required. Of course if energy and space limitations allow, also other types of controllers may be used in the sensor systems 200B according to the invention. The input received by the controller 260 may be used to, for example, change the status or way of working of the sensor system 200B dependent on the received input. The controller 260 used in the embodiment of the invention may, for example, ensure that the sensor 210 takes a sensed value $x_T$, $x_P$ at each time trigger t1, t2, . . . generated by the timer 230 and that the sensed value $x_T$, $x_P$ (possibly including the trigger number time1, time2, . . . ) is subsequently stored in the storage element 220. The storage element 220 may again, for example, be a shift register 220 in which the sensed values $x_T$, $x_P$ are sequentially stored as they are measured by the sensor 210. The controller 260 may, for example, be constituted of one or more logic blocks 262, 264 as only very limited and basic control seems to be required for the operation of the sensor system 200B. Furthermore, constituting the controller 260 of a few logic blocks 262, 264 only would minimize the power required to run the sensor system 200B and would allow the sensor system 200B, including controller 260, to be contained in such small containers 400, 410. Of course, when power and dimension requirements are met to allow the sensor system 200B to operate during the predefined time duration, any controller system 260 or microcontroller 260 may be used as the controller 260 in the sensor system 200B.

In an embodiment of the sensor system 200B as shown in FIG. 2B, the controller 260 is coupled to the antenna 250 via a double headed arrow. This double headed arrow indicates that there might be a two-way communication between the controller 260 and the antenna 250 such that the controller 260 is configured to communicate via the antenna. The controller 260 may, for example, be configured for communicating the stored sensed values xT, xP from the storage element 220 to the outside—for example, a remote computer (not shown) used for the analysis of the data. When the sensor system 200B has been working in the remote environment 100 and has been harvested back from the remote environment 100, the controller 260 may be triggered, for example, using a "release storage trigger" signal (not shown) such that the sequence of sensed values xT, xP, possibly together with the corresponding trigger number t1, t2, . . . , is transmitted via the antenna 250. Alternatively or additionally, the controller 260 may be configured for receiving configurable parameters via the antenna 250 for configuring an operation of the sensor system 200B. The sensor system 200B may be configured using specific parameter settings which may, for example, be stored in the controller 260 or at a specific predefined place in the storage element 220. Such parameter settings may, for example, be the duration of the predetermined time interval Δt between two subsequent triggers t1, t2, . . . and/or the predefined time duration during which the sensor system 200B is to be operated.

Using the antenna 250 both for charging the energy storage 220 and for communication of the controller 260 with the outside further reduces the overall elements required to allow the sensor system 200B to function, which further contributes to the miniaturization and cost reduction of the sensor system 200B according to the invention.

In an embodiment, the mote can be configured or re-configured. The controller may be configured to receive over the antenna configurable parameters. The configurable parameters may define a basic functionality of mote. The basic functionality may include executing a different time sequence and/or selecting an environmental parameter for measurements. This is an advantageous feature of the motes-system because it allows having different groups of motes programmed with a different behavior, for example, one group of motes measures temperature and another group of motes measures pressure, or something else. When the two groups of motes are used (and charged) together coherent data is obtained given information over both aspects; in this example, temperature, and pressure. Having additional data, which is however synchronized reconstructing (e.g. mapping) an unknown environment is easier, e.g., requiring fewer computational resources.

Of course different architectures of the second embodiment of the sensor system 200B are possible without diverting from the scope of the invention. For example, in the embodiment shown in FIG. 2B all communication inside the sensor system 200B is arranged via the controller 260 which is indicated with the double headed arrows going from the controller 260 to each of the other elements of the sensor system 200B. Of course, not all communication need to goes through the controller 260 as alternatively was shown in the first embodiment of the sensor system 200A (shown in FIG. 2A). Again, the power distribution in the sensor system 200B shown in FIG. 2B is illustrated by the connecting dash-dotted lines between the energy storage 240 and the remainder of the elements of the sensor system 200B.

Figure 4A:
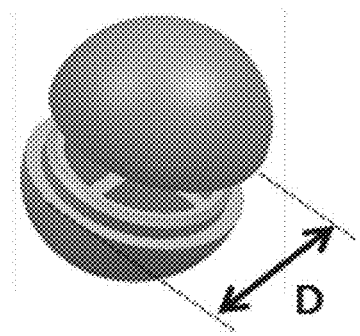
FIGS. 4A and 4B show possible containers for the sensor system according to the invention.
Figure 4B:
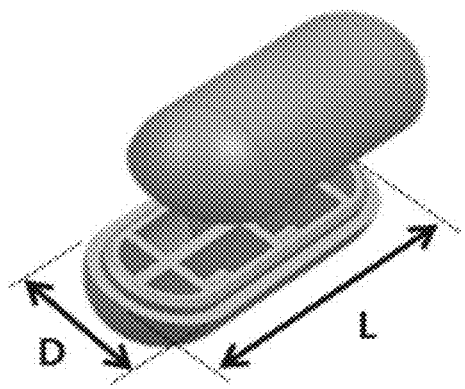

Sensor systems 200A, 200B as shown in FIGS. 2A and 2B may be contained in a container 400, 410 (see FIGS. 4A and 4B) to constitute a mote 300, 310. The material chosen for the container 400, 410 depends on the liquid through which the mote 300, 310 is designed to float and depends on the chemical composition of the liquid such that the sensor system 200A, 200B is protected from the environment it floats in while still being able to sense the environmental parameter T, P, pH, ρ. As an alternative to the containers 400, 410 as shown in FIGS. 4A and 4B, the container may be constituted by melting a material such as plastic or a resin, and submerge the sensor system 200A, 200B in the molten material after which the molten material is hardened. Using such a container would encapsulate the sensor system 200A, 200B and fully protect the sensor system 200A, 200B from the surrounding environment. And because both the charging and initiation of the sensor system 200A, 200B is done wirelessly, such mote 300, 310 comprising an encapsulated sensor system 200A, 200B may be able to withstand very harsh environments.

Figure 3:
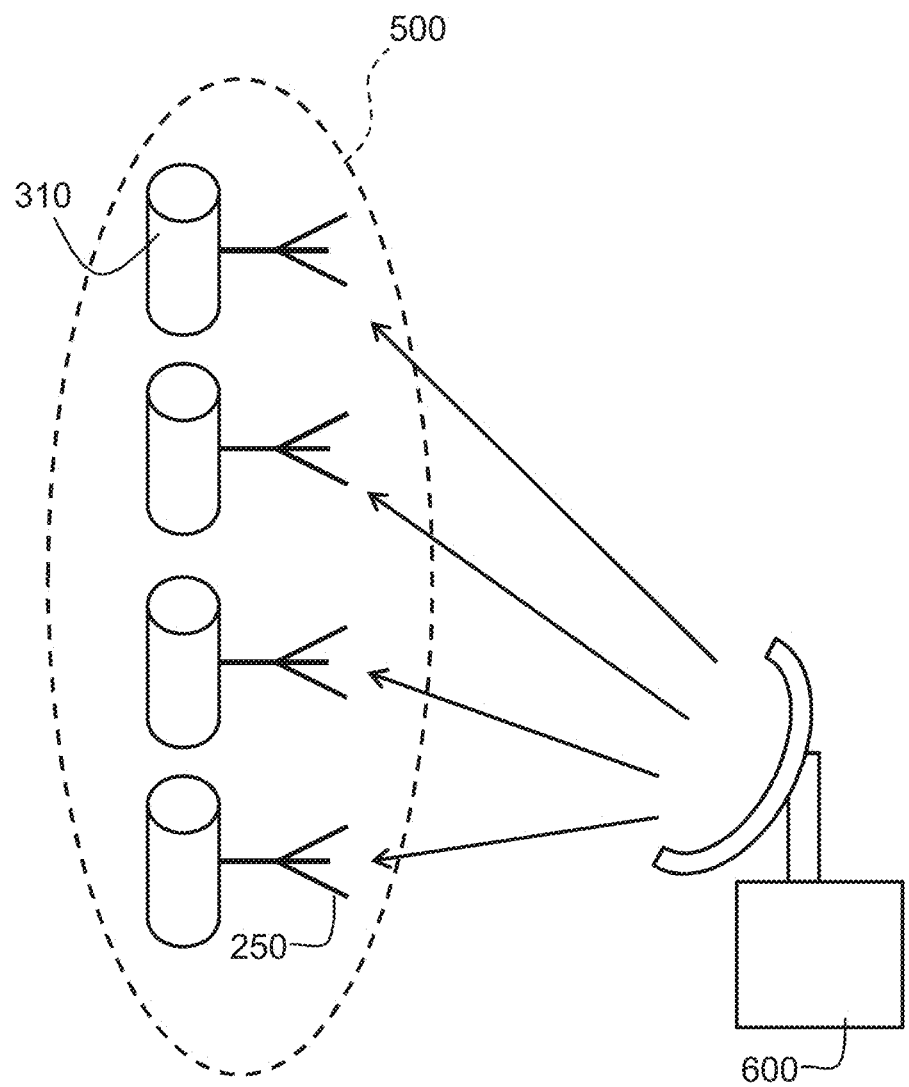
FIG. 3 shows a schematic view of a motes-system comprising a plurality of motes which can be charged and synchronized simultaneously.

FIG. 3 shows a schematic view of a motes-system 500 comprising a plurality of motes 310 which can be charged and synchronized simultaneously. For charging a generator 600 may be in the vicinity of the plurality of motes 310 for emitting the electro-magnetic radiation. The motes 310 each comprise the sensor system 200A, 200B (see FIGS. 2A and 2B) according to the invention, comprising an antenna 250 configured for capturing part of the electro-magnetic radiation emitted by the generator 600 and using the captured part of the electro-magnetic radiation for charging energy storage 240 in each of the sensor systems 200A, 200B. In a preferred embodiment, the motes 310 are configured for starting the sequence of time triggers t1, t2, . . . and the sequence of sensed values $x_T$, $x_P$ at the time the energy storage 240 is being charged or at the time the energy storage 240 is fully charged. In such a motes-system 500, each of the individual motes 310 are simultaneously charged and initiated via the generator 600 such that each of the sensor values $x_T$, $x_P$ stored in corresponding positions in the storage element 220 of each of the individual motes 310 in the motes-system 50 is measured substantially at the same time.

For mapping the remote environment 100, the motes-system 500 comprising a plurality of synchronized motes 310 are injected into the remote environment 100 and are configured to sense the environmental parameter T, P, pH, ρ at substantially the same time triggers t1, t2, . . . generated by each individual timer 230 of each of the individual motes 310. When the plurality of motes 310 are subsequently harvested, the sequence of sensed values $x_T$, $x_P$ may be analyzed to determine information about the remote environment 100. When including, next to the sequence of sensed values $x_T$, $x_P$, also the overall migration time necessary for the individual mote 310 to get from the injection point to the extraction point, relatively detailed information may be gathered from the data about the extent of the remote environment. More information about possible measurement principles may be found in the co-owned and co-pending patent application "Method and system for mapping a three-dimensional structure using motes", with NL application number N2012483, which was filed at the same date at the Dutch patent office and which is incorporated herein by reference.

FIGS. 4A and 4B show possible containers 400, 410 for the motes 300, 310 according to the invention. As indicated above, the motes 300, 310 according to the invention may be used in harsh environments 100 and so may require a specific container 400, 410 for protecting the motes 300, 310 while migrating through the harsh environment 100. Furthermore, the containers 400, 410 may protect the motes from mechanical impact of moving parts when they have to pass pumps used, for example, to harvest crude oil from the oil well 100. Finally, the containers 400, 410 may be used to ensure that the volumetric mass density of a mote 300, 310 substantially equals the volumetric mass density of the liquid. This ensures that the motes 300, 310 preferably neither sink in the liquid nor rise; as a result the motes 300, 310 will more easily enter all parts of the remote environment 100.

The specific density of the mote controls their behavior according to the fluid dynamics. A suitable specific density or specific gravity may be achieved by choosing a suitable material for the container, e.g., casing, and their wall thickness and shape based on the design of a mote and volumetric calculations. In an embodiment, the container comprises ballast weight to control the density of the mote. In an embodiment, the density of the mote equals the density of water.

The maximum outer dimensions D of the container 400 shown in FIG. 4A is a diameter indicated with the double-headed and should be less than 10 millimeter. The maximum outer dimension L of the container 410 shown in FIG. 4B is a length parameter measured along the longitudinal axis of the elongated container 410 which should be less than 10 millimeter.

The motes may be used in a method for collecting sensor data from an environment, the environment having an injection point (130), and an extraction point (140). The method may comprise charging a plurality of motes via electro-magnetic radiation, thereby initiating in the plurality of motes, measuring of at least one environmental parameter (T, P, pH, ρ) substantially at the time of each of a plurality of time triggers (t1, t2, . . . ) and for generating a corresponding sensed value ($x_T$, $x_P$) and storing the sensed value ($x_T$, $x_P$) onto the storage element (220), generating a sequence of sensed values ($x_T$, $x_P$), the plurality of time triggers being separated by a predetermined time interval (Δt)

injecting via an injection point (130) the plurality of motes into the environment (100) using a stream of liquid, allowing the plurality of motes (300) to migrate through the environment via the injected liquid from the injection point (130) to the extraction point (140), harvesting at least part of the plurality of motes (300) from the environment (100) via the extraction point (140)

extracting the stored sequences of sensed values ($x_T$, $x_P$) from the harvested motes.

In an embodiment, the method may further comprise placing harvested motes inside a tank containing liquid at a specific predefined temperature. In this way the time at which the mote is harvested is registered.

The environment may be any environment in which motes may be inserted and extracted using a liquid. For example the environment may be an oil well, the injection point is an injection pipe, and the extraction point is an extraction pipe. The environment can be, for example, a sewer system, a water distributing network, an oil reservoir, etc. The inserting and extraction point can be, for example, an inserting port or pipe or well, etc.

FIG. 5 shows possible data content of the storage element 220 of a sensor system 200A, 200B according to the invention. The storage element 220 may be a relatively simple shift register 220 for sequentially storing the stored values $x_T$, $x_P$, possible together with the trigger number time1, time2, . . . . As indicated before, any other type of storage element 220 apart from a shift register 220 may be used, as long as the dimensions of the storage element 220 and the energy consumption of the storage element 220 allow the operation of the mote 300, 310 during the predefined time duration.

In FIG. 5, the left-hand column comprises a tabled listing of trigger values time1, time2, . . . is shown as a relatively simple sequence of numbers. Each of the trigger values time1, time2, . . . which is listed in the table are generated separated by the predetermined time interval Δt. As indicated before, this predetermined time interval Δt may be configurable and may, for example, ensure that the environmental parameter is measured every 5 minutes, or every 10 minutes, or every 15 minutes, or every half hour, or every hour.

In FIG. 5, the right-hand column comprises the sensed values $x_T$, $x_P$ which are temperature values $x_T$ which represent the ambient temperature at the immediate vicinity of the sensor system 200A, 200B at the corresponding time values time1, time2, . . . . In the current example, the temperature value $x_T$ is indicated in Kelvin. The sequence shown, for example, represents a pre-conditioned state in which the motes 300, 310 are kept in a tank containing ice-water at 0 degrees Celsius (approximately 273 degrees Kelvin). Next, the motes 300, 310 are inserted into boiling water which is injected into the remote environment 100 which can be seen from the stored data in that the temperature of the mote 300, 310 immediately rises to 100 degrees Celsius (or approximately 373 degrees Kelvin). Next, the cooling of the mote 300, 310 is shown in the subsequent sensed values $x_T$ in the listing of FIG. 5. This cooling sequence depends on the exact path taken through the remote environment 100 by the individual motes 300, 310. By collecting a plurality motes 300, 310 and by analyzing the different cooling sequences of the individual motes 300, 310 an extent of the remote environment may be determined.

Although the data content shown in FIG. 5 includes both the trigger number time1, time2, . . . and the sensed value $x_T$, $x_P$, the trigger number time1, time2, . . . is optional as the actual time the measurements are taken may already be defined by the position in the sequence of sensed values $x_T$, $x_P$ as stored in the storage element 220.

Summarizing, the invention provides a sensor system 200), mote and a motes-system. The sensor system is configured for being contained in a container having a maximum outer dimension less than 10 millimeter and for sensing at least one environmental parameter T, P, pH, ρ. The sensor system comprises at least one sensor 210 configured for measuring the at least one environmental parameter and for generating a sensed value $x_T$, $x_P$. The sensor system comprises a storage element 220 and a timer 230 in which the at least one sensor is configured to measuring the at least one environmental parameter at each time triggers t1, t2, . . . from the timer and for storing a sensed value $x_T$, $x_P$. The sensor system further comprises an energy storage 240 comprising a chargeable capacitor 240 being chargeable via electro-magnetic radiation of a predefined frequency, and wherein the sensor system is configured to initiate a sequence of sensed values when the energy storage is charged or is being charged.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A first sensor system configured for being contained in a container and for sensing at least one environmental parameter, the first sensor system comprising:
    at least one sensor configured for measuring the at least one environmental parameter and for generating a sensed value representing the at least one environmental parameter,
    a storage element for storing the sensed value,
    a first timer for generating a plurality of time triggers separated by a predetermined time interval,
    a first energy storage for supplying at least the at least one sensor, first timer and storage element with power to enable operation of the first sensor system during a predefined time duration, wherein the first energy storage comprises a chargeable capacitor being chargeable via electro-magnetic radiation of a predefined frequency, and
    an antenna for receiving the electro-magnetic radiation for charging the first energy storage,
    wherein:
        initialization of the first timer is based on a charge state of the first energy storage,
        the predetermined time interval separating the plurality of time triggers is configurable and independent from the charge state of the first energy storage,
        the at least one sensor is configured to generate a sequence of sensed values by measuring the at least one environmental parameter substantially at the time of each of the plurality of time triggers, generating a corresponding sensed value, and storing the sensed value onto the storage element,
        the electro-magnetic radiation can be simultaneously applied to a second energy storage of a second sensor system, the second energy storage being chargeable via the electro-magnetic radiation, the second sensor system having a second timer for generating a second plurality of time triggers separated by the predetermined time interval, such that:
            the first timer of the first sensor system is substantially synchronized with the second timer of the second sensor system, and
            the sequence of sensed values is substantially synchronized with a second sequence of sensed values from the second sensor system.

2. The first sensor system according to claim 1, wherein the initialization of the first timer comprises resetting the first timer.

3. The first sensor system according to claim 2, wherein the first timer comprises an oscillator and a counter and wherein the resetting of the first timer comprises resetting the counter.

4. The first sensor system according to claim 3, wherein the first sensor system is configured for storing a trigger number together with each sensed value, the trigger number being generated by the first timer and indicating a number of time triggers generated by the first timer since the resetting of the first timer.

5. The first sensor system according to claim 1, wherein the first sensor system further comprises a controller for controlling the operation of the first sensor system.

6. The first sensor system according to claim 5, wherein the controller is constituted of one or more logic blocks.

7. The first sensor system according to claim 5, wherein the controller is coupled to the antenna and is configured to communicate via the antenna.

8. The first sensor system according to claim 7, wherein the controller is configured for communicating the stored sensed values.

9. The first sensor system according to claim 7, wherein the controller is configured for receiving configurable parameters via the antenna for determining an operation of the first sensor system.

10. The first sensor system according to claim 7, wherein the predetermined time interval is a configurable parameter.

11. The first sensor system according to claim 1, wherein the at least one environmental parameter is selected from a list comprising at least temperature pressure, acidity, and conductivity.

12. The first sensor system according to claim 1, wherein the predefined time duration is at least 24 hours.

13. A first mote comprising the first sensor system according to claim 1 contained in the container, wherein the volumetric mass density of the first mote is substantially equal to the volumetric mass density of a predefined liquid.

14. A motes-system comprising the first mote according to claim 13, and a second mote comprising the second sensor system.

15. A method for collecting sensor data from an environment, the environment having an injection point, and an extraction point, the method comprising:
- applying the electro-magnetic radiation simultaneously to the first mote and the second mote according to claim 14, thereby substantially synchronizing the first timer of the first mote and the second timer of the second mote,
- injecting via an injection point the first mote and the second mote into the environment using a stream of liquid,
- allowing the first mote and the second mote to migrate through the environment via the injected liquid from the injection point to the extraction point,
- harvesting at least part of the first mote and the second mote from the environment via the extraction point, and
- extracting the stored sequence of sensed values from the harvested motes.

16. The method for collecting sensor data from an environment as in claim 15, comprising
- placing the harvested motes inside a tank containing liquid at a specific predefined temperature.

17. The method for collecting sensor data from an environment as in claim 15 wherein the environment is an oil well, water distribution system, sewer system, or a reservoir for a liquid.

* * * * *